US011643640B2

(12) United States Patent
Ikegami

(10) Patent No.: US 11,643,640 B2
(45) Date of Patent: May 9, 2023

(54) RIFT VALLEY FEVER VACCINE

(71) Applicant: BOARD OF REGENTS, THE UNIVERSITY OF TEXAS SYSTEM, Austin, TX (US)

(72) Inventor: Tetsuro Ikegami, Galveston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 362 days.

(21) Appl. No.: 17/067,144

(22) Filed: Oct. 9, 2020

(65) Prior Publication Data

US 2021/0108181 A1 Apr. 15, 2021

Related U.S. Application Data

(60) Provisional application No. 62/912,957, filed on Oct. 9, 2019.

(51) Int. Cl.
*C12N 7/00* (2006.01)
*A61K 39/12* (2006.01)

(52) U.S. Cl.
CPC ................ *C12N 7/00* (2013.01); *A61K 39/12* (2013.01); *C12N 2760/12021* (2013.01); *C12N 2760/12034* (2013.01)

(58) Field of Classification Search
None
See application file for complete search history.

(56) References Cited

U.S. PATENT DOCUMENTS

2021/0108181 A1* 4/2021 Ikegami ............... C07K 14/005

FOREIGN PATENT DOCUMENTS

WO WO 2014/189372 * 11/2014

OTHER PUBLICATIONS

Alignment of SEQ ID No. 1 with GenEmbl db access No. MF593928 by Ly et al. 2017.*
Alignment of SEQ ID No. 3 with GenEmbl db access No. MF593930 by Ly et al. 2017.*
Alignment of SEQ ID No. 4 with GenEmbl db access No. MF593929 by Ly et al. 2017.*
Ly et al. (PLoS ONE. 2017; 12 (9): e0185194).*
Lihoradova et al. (Journal of Virology. 2012; 86 (14): 7650-7661).*
Pittman et al. (Vaccine. 2016; 34: 523-530).*
Kalveram et al. (JoVE (Journal of Visualized Experiments) 57 (2011): e3400).*
Cheng et al. (JoVE (Journal of Visualized Experiments) 78 (2013): e50662).*

* cited by examiner

*Primary Examiner* — Shanon A. Foley

(57) ABSTRACT

Certain embodiments are directed to an improved RVF vaccine for human use, and method for producing the same.

16 Claims, 7 Drawing Sheets

Specification includes a Sequence Listing.

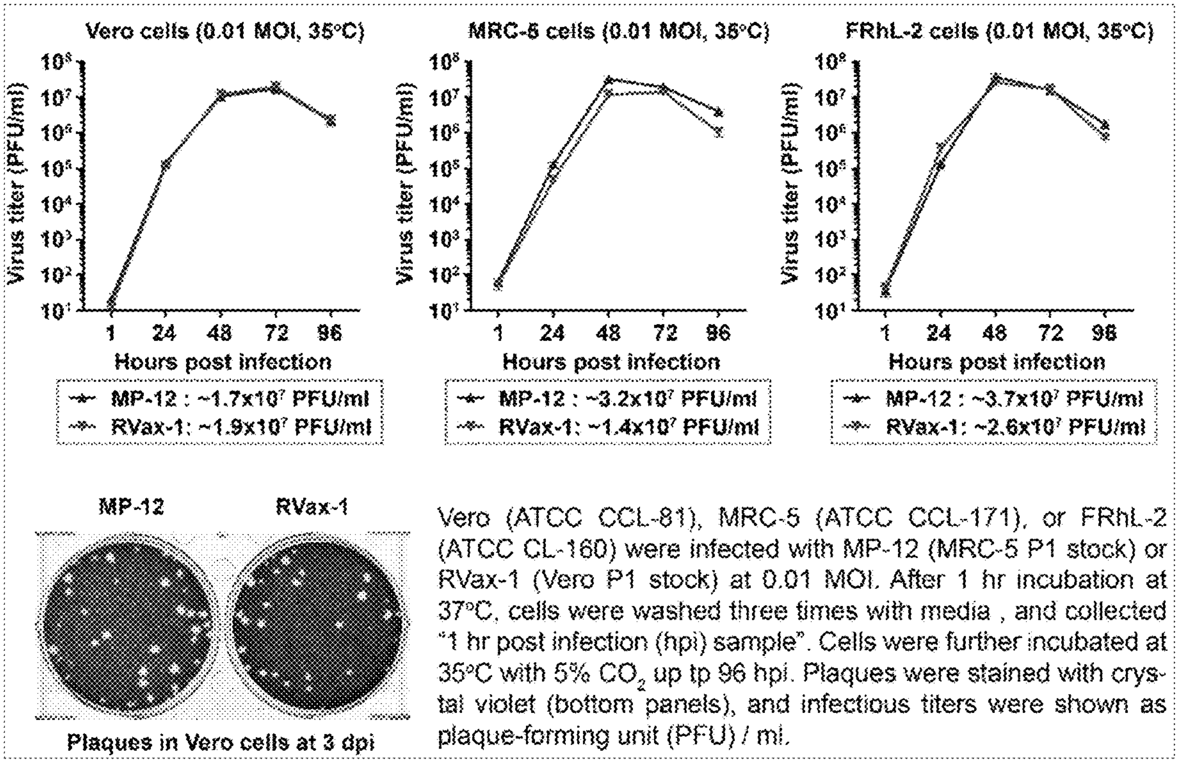

FIG. 1

Vero (ATCC CCL-81), MRC-5 (ATCC CCL-171), or FRhL-2 (ATCC CL-160) were infected with MP-12 (MRC-5 P1 stock) or RVax-1 (Vero P1 stock) at 0.01 MOI. After 1 hr incubation at 37°C, cells were washed three times with media, and collected "1 hr post infection (hpi) sample". Cells were further incubated at 35°C with 5% $CO_2$ up tp 96 hpi. Plaques were stained with crystal violet (bottom panels), and infectious titers were shown as plaque-forming unit (PFU) / ml.

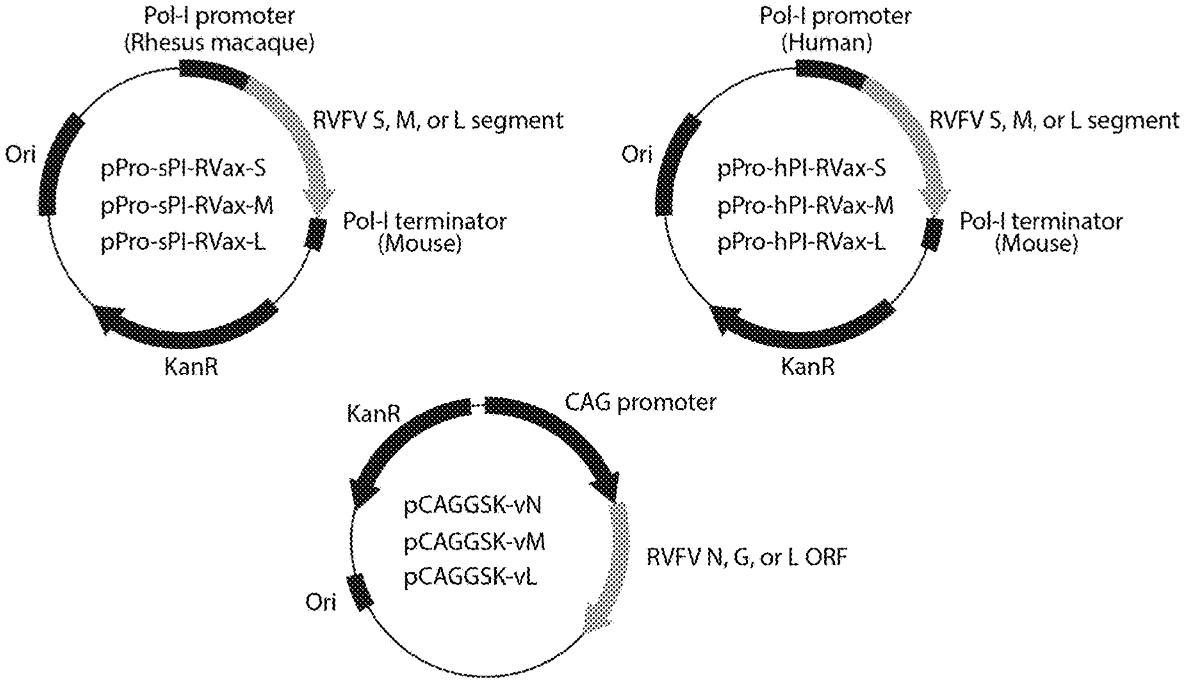

FIG. 2

Precursor rRNA promoter sequences / Homo sapiens = SEQ ID NO:5; Macaca mulatta = SEQ ID NO:6; Vero cells = SEQ ID NO:7

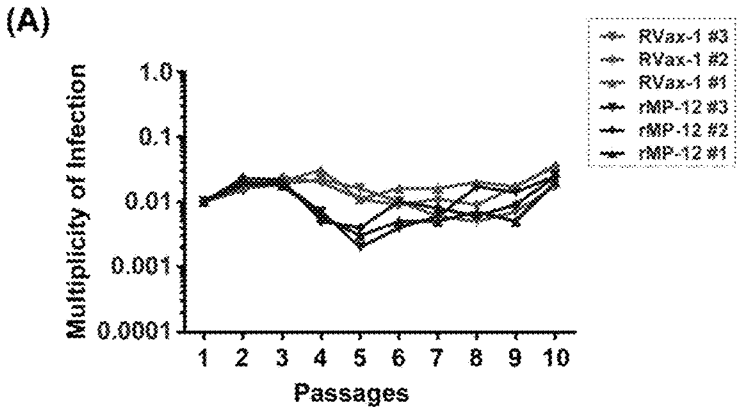
FIG. 7A
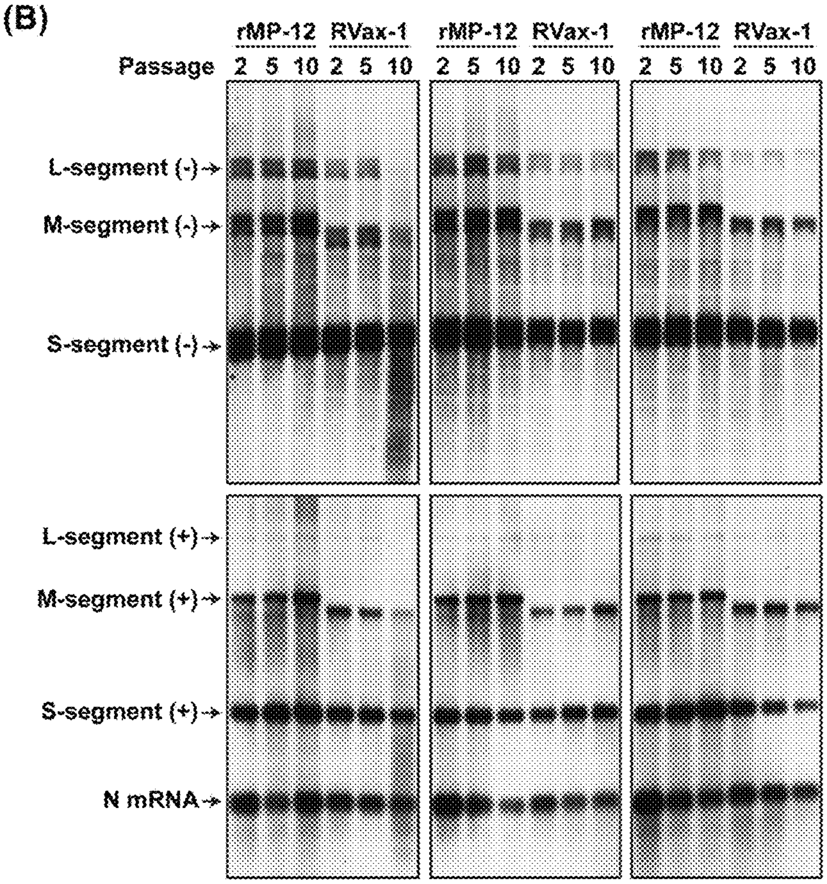
FIG. 7B
(C)
| | Changes of silent mutations of RVax-1 | | |
|---|---|---|---|
| L-segment (326 silent mut.) | 0/326 | 0/326 | 0/326 |
| M-segment (167 silent mut.) | 0/167 | 0/167 | 0/167 |
| S-segment (73 silent mut.) | 0/73 | 0/73 | 0/73 |
| Passages: | [2] | [5] | [10] |
FIG. 7C

RIFT VALLEY FEVER VACCINE

PRIORITY CLAIM

The present application claims priority to U.S. Provisional Application No. 62/912,957 filed Oct. 9, 2019, the disclosure of which is incorporated herein by reference.

STATEMENT REGARDING FEDERALLY FUNDED RESEARCH

None.

REFERENCE TO SEQUENCE LISTING

A sequence listing required by 37 CFR 1.821-1.825 is being submitted electronically with this application. The sequence listing is incorporated herein by reference.

BACKGROUND

Rift Valley fever (RVF) is a mosquito-borne zoonotic viral disease endemic to Africa and the Arabian Peninsula. The disease is characterized by high-rates of abortions and fetal malformations in pregnant ewes or cattle, as well as causing hemorrhagic fever, neurologic disorders, and blindness in humans. The causative agent, Rift Valley fever *Phlebovirus* (RVFV; family Phenuiviridae, genus *Phlebovirus*) is a negative-sense (or ambi-sense) RNA virus with a tripartite genome consisting of Large (L)-, Medium (M)-, and Small (S)-segments. In the U.S., RVFV is classified as a Category A Priority Pathogen by the National Institute of Health, and as an overlap select agent by the U.S. Department of Health and Human Services and Agriculture. Vaccination is the primary countermeasure against the threat. Stockpiling of effective RVF vaccine for animals and humans is thus important, although actions may be taken only after a realistic threat is indicated for humans or animals. A live-attenuated MP-12 vaccine is conditionally licensed for emergency veterinary use in the U.S., and is also an immunogenic RVF vaccine candidate for humans. There are no licensed RVF vaccines for human use, which listed RVFV as one of the Blueprint Priority diseases by the World Health Organization.

Human infections typically occur either from an infected mosquito bite, percutaneous/aerosol exposure during the slaughter of infected animals, or via contact with aborted fetal materials. Human RVF disease is primarily a self-limiting febrile illness that in a small percentage (about 1-2%) of cases can progress to more serious and potentially lethal complications including hepatitis, delayed onset encephalitis, retinitis, blindness, or a hemorrhagic syndrome with a hospitalized case fatality of 10-20% (Madani et al., *Clin. Infect. Dis.* 37:1084-92, 2003; McIntosh et al., *S. Afr. Med. J.* 5:803-06, 1980). Excessively heavy rainfall in semi-arid regions often precedes large periodic outbreaks of RVF virus activity, allowing for the abundant emergence of transovarially infected *Aedes* spp. mosquitoes and subsequent initiation of an outbreak by transmission of virus to livestock and humans via infected mosquito feeding (Linthicum et al., *Science* 285:397-400, 1999; Swanepoel et al., *Contributions to Epidemiology and Biostatistics* 3:83-91, 1981). The association with abnormally heavy rains provides some ability to predict periods and regions of high disease risk, which in turn provides a potential window of opportunity for targeted vaccination programs if a safe, inexpensive and highly efficacious single dose vaccine were available.

The ability of RVF virus to cross international and geographic boundaries and strain veterinary and public health infrastructures is well documented. In 1977, RVF virus was reported for the first time north of the Sahara desert where an extremely large outbreak affecting more than 200,000 people occurred along the Nile River basin in Egypt (Meegan et al., *Contributions to Epidemiology and Biostatistics* 3:100-13, 1981). Approximately ten years later in 1987, a large outbreak occurred in western Africa along the border of Mauritania and Senegal affecting an estimated 89,000 individuals (Jouan et al., *Res. Virol.* 140:175-86, 1989). Later, the virus was isolated for the first time outside of Africa (across the Red sea) in Saudi Arabia and Yemen and was found to be the cause of a large epizootic/epidemic in 2000 with an estimated 2000 human cases and 245 deaths (Anonymous, *Morb. Mortal. Wkly. Rep.* 49:982-5, 2000; Centers for Disease Control and Prevention, *Morb. Mortal. Wkly. Rep.* 49:1065-1066, 2000; Shoemaker et al., *Emerg. Infect. Dis.* 8:1415-1420, 2002).

Most recently, in late 2006 to early 2007, following heavy rainfall in eastern Africa, RVF virus emerged as the cause of a widespread outbreak that eventually resulted in 1062 reported human cases and 315 reported deaths. Associated with the outbreak were substantial economic losses among livestock in southern Somalia, Kenya, and northern Tanzania (Anonymous, *Morb. Mortal. Wkly. Rep.* 56:73-6, 2007). The ability of RVF virus to cause explosive outbreaks in previously unaffected regions accompanied by high morbidity and mortality during RVF epizootics/epidemics highlights the importance of developing safe and efficacious vaccines for this significant veterinary and public health threat.

Two RVF candidate vaccines have been tested in clinical trials in humans. The first human RVF vaccine candidate was TSI-GSD-200, which is a formalin-inactivated pathogenic RVFV Entebbe strain. This vaccine has weak immunogenicity, and requires at least three doses to induce minimal protective immunity and also additional booster dose to maintain the protective status for longer period. The second candidate was a live-attenuated MP-12 strain. MP-12 can induce protective immunity in humans with a single dose, without any major adverse effects in tested human subjects (~100). In contrast, MP-12 can still cause mild to moderate liver necrosis in newborn lambs or goat kids, and fetal malformation in pregnant ewes via injection early in pregnancy. Due to inconsistent safety profiles among tested animal species and ages, it is still not fully conclusive that MP-12 is indeed safe in humans in any ages or health status. Currently, high risk personnel for RVF infection receive vaccination with TSI-GSD-200, rather than MP-12.

The second generation MP-12 candidate vaccine, rMP12-ΔNSm21/384, which lacks 78-kD/NSm genes, was generated by using the reverse genetics, and the immunogenicity was shown to be as strong as parental MP-12 vaccine in sheep and cattle. Deletion of 78-kD/NSm genes from RVFV does not affect the viral replication, but can reduce the dissemination within infected mosquitoes. Nevertheless, the L- and S-segment are identical to those of MP-12 strain, which does not alter the outcome of viable reassortant formation via parental MP-12 M-segment.

There remains a need for additional safe and effective RVFV vaccines.

SUMMARY

The problem of an effective vaccine to be used to control RVFV infections that minimizes or reduces reassortant formation is addressed by development of a third generation MP-12 vaccine, RVax-1 (rMP12-GM50ΔNSm21/384), which is highly suitable for use in humans in endemic area. RVax-1 maintains immunogenicity, contains attenuated L, M, and S segments, and is capable to being traced, which provides a solution to the immunogenicity and reassortant problems associated with current RVFV vaccines.

A prototype was previously generated and reported as rMP12-GM50 strain (Ly et al., *Vaccine* 35: 6634-42, 2017, L segment (SEQ ID NO:1; M segment SEQ ID NO:2; and S segment SEQ ID NO:3). The rMP12-GM50 strain encodes silent mutations throughout open reading frames (ORF) of viral genome: N ORF (36 nt mutations), NSs ORF (37 nt mutations), 78-kD/NSm ORF (22 nt mutations: not including overlapped Gn ORF), Gn ORF (82 nt mutations), Gc ORF (83 nt mutations), and L ORF (326 mutations). The prototype has a total of 588 nt unique mutations introduced into the MP12 strain. To evaluate the attenuation of L, M, or S segment of this prototype, the inventor generated recombinant pathogenic RVFV ZH501 strain (rZH501; S, M and L segments of the ZH501 strain are deposited under GenBank Accession Nos. DQ380149, DQ380200 and DQ375406, respectively) encoding either of the L, M, or S segment of this prototype strain. As a result, it was found that L segment and S segment were more attenuated than those of parental MP-12 strain, whereas the attenuation of M-segment was similar to that of parental MP-12 strain. Preliminary immunogenicity testing using a mouse model indicated that the prototype retains strong immunogenicity similar to that of parental MP-12 strain.

To design an improved RVF vaccine for human use, the M-segment of rMP12-GM50 was modified to truncate the 78-kD/NSm gene expression (SEQ ID NO:4). The resulting strain was designated as GM50ΔNSm21/384 (RVax-1) the strain comprising an L-segment having a nucleotide sequence of SEQ ID NO:1, an M-segment having a nucleotide sequence of SEQ ID NO:4, and a S-segment having a nucleotide sequence of SEQ ID NO:3. The RVax-1 strain was successfully rescued by using reverse genetics, and the viable replication was confirmed in Vero, MRC-5, and FRhL-2 cells. The RVax-1 encodes total 566 silent mutations, and a deletion from nucleotides 21 to 384 within the M-segment (SEQ ID NO:4).

The RVax-1 retains strong immunogenicity similar to original MP-12 vaccine. The MP-12 vaccine is highly immunogenic as a single dose, and well attenuated. It was shown that a deletion of NSs gene in MP-12 backbone led to a much less immunogenic strain (e.g., R566 strain). RVax-1 encodes a number of silent mutations, which can modestly attenuate original MP-12 strain without affecting the original immunogenicity. RVax-1 is attenuated via L-, M-, and S-segments. For safe use in humans, RVax-1 encodes strengthened attenuation phenotypes via all the L-, M-, and S-segment. This change can diminish viral replication capability of RVax-1 and the reassortant strains with wt RVFV in vivo. Furthermore, the RVax-1 encodes a genetic signature that is traceable. Due to a lack of 78-kD/NSm gene, any reassortant strain carrying RVax-1 M-segment will not be spread via mosquito vectors. Meanwhile, other reassortant strains carrying wt RVFV M-segment plus S and/or L segment of RVax-1 are highly attenuated in animals and humans. Even if such strains are retained in mosquito populations, the presence can be genetically traced through the variations present in RVax-1, while stimulating natural immunization of animal populations via such mosquitoes.

RVax-1 was rescued via reverse genetics, and the replication kinetics was compared with that of parental MP-12 strain. African monkey kidney cells (Vero, ATCC CCL-81), human lung diploid cells (MRC-5, ATCC CCL-171), or rhesus monkey lung cells (FRhL-2, ATCC CL-160) were infected with MP-12 or RVax-1 at 0.01 MOI at 37° C. After 1 hr incubation at 37° C., cells were washed three times with media, and further incubated at 35° C. The temperature of 35° C. was selected for the vaccine rather than 37° C. (the temperature of master seed preparation) because MP-12 IND vaccine was manufactured at 35° C. RVax-1 formed plaques indistinguishable from MP-12. Moreover, the replication kinetics of RVax-1 and MP-12 were nearly identical in Vero and FRhL-2 cells, whereas RVax-1 replication was slightly less efficient than MP-12 in MRC-5 cells. The result indicated that RVax-1 makes a similar yield to that of MP-12 in culture cells.

Novel reverse genetics system, which does not use any rodent-derived cell lines, was newly formulated for the creation of RVax-1 master seed. Certain embodiments are directed to a novel reverse genetics to rescue infectious clone of RVFV MP-12 strain directly from Vero cells. The cDNA of full-length antiviral-sense RVFV L-, M-, or S-segment were cloned immediate downstream of Human or Rhesus macaque (*Macaca mulatta*) RNA polymerase I promoter and upstream of mouse RNA polymerase I terminator of modified pProT7 plasmid (pProT7K-PI, kanamycin-resistant (pProK-hPI plasmid (human Pol-I) or pProK-sPI (simian Pol-I))). The cDNA of RVFV N, M, or L open reading frame (ORF) were cloned under chicken β-actin promoter of modified pCAGGS plasmid (pCAGGSK, kanamycin-resistant). Vero cells were then co-transfected with six different plasmids listed above. Transfected Vero cells started showing cytopathic effects (CPE) similar to virus-plaques by 3 days post transfection. Transfer of culture supernatants into fresh Vero cells resulted in extensive CPE by 3 days post infection. Direct recovery of RVFV MP-12 strain in Vero cells allows straightforward manufacturing of RVFV vaccine candidates for human use, without concerning contaminants derived from rodent cell lines.

Certain embodiments are directed to a non-rodent cell comprising (i) cDNA of full-length sense RVFV L segment, (ii) cDNA of full-length sense RVFV M segment, (iii) cDNA of full-length sense RVFV S segment, (iv) cDNA of RVFV N open reading frame (ORF), (v) cDNA of RVFV M ORF, and cDNA of RVFV L ORF. Wherein the M segment (SEQ ID NO:4) includes 3' UTR (46 nt)+M ORF (3204 nt)+5' UTR (271 nt), and the L segment includes 3' UTR (18 nt)+L ORF (6279 nt)+5' UTR (107 nt). The full-length S, M, and L-segment sequences are derived from SEQ ID NO: 3, 4, and 1, respectively. Wherein the ORF sequences of N, M, and L are derived from those of authentic MP-12 strain (GenBank #DQ380154.1, DQ380208.1, and DQ375404.1, respectively. In certain aspects cDNAs (i), (ii), and (iii) are, independently, immediately downstream of human or non-human primate RNA polymerase I promoter and upstream of mouse RNA polymerase I terminator. In certain aspects ORFs (iv), (v) and (vi) are under independent control of a chicken β-actin promoter.

Certain embodiments are directed generally to compositions and methods related to attenuated RVFV and forming recombinant vector encoding the same.

The RVFV L-segment can have a nucleotide sequence that is, is at least or is about 90, 91, 92, 93, 94, 95, 96, 97, 98, 99, to 100% identical to the nucleic acid sequence of SEQ ID NO:1. In certain instances the L segment contains 326 single nucleotide variants. In certain aspects, the L segment contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, or 326 variant nucleotides at positions 48, 54, 105, 108, 150, 156, 201, 205, 207, 255, 258, 292, 294, 298, 300, 343, 344, 348, 405, 408, 450, 453, 498, 501, 555, 558, 600, 601, 602, 648, 654, 693, 697, 698, 745, 746, 750, 801, 804, 807, 850, 851, 852, 853, 854, 903, 906, 945, 946, 948, 954, 996, 999, 1047, 1050, 1098, 1101, 1152, 1155, 1203, 1206, 1249, 1250, 1260, 1305, 1308, 1342, 1343, 1347, 1398, 1399, 1401, 1452, 1455, 1456, 1458, 1500, 1503, 1545, 1548, 1551, 1596, 1602, 1650, 1656, 1704, 1707, 1753, 1755, 1758, 1789, 1791, 1794, 1800, 1849, 1850, 1851, 1852, 1854, 1899, 1900, 1901, 1944, 1947, 1956, 2004, 2007, 2049, 2052, 2103, 2106, 2148, 2149, 2151, 2202, 2208, 2248, 2250, 2253, 2256, 2295, 2301, 2355, 2358, 2403, 2406, 2448, 2452, 2454, 2505, 2508, 2548, 2549, 2553, 2554, 2556, 2598, 2607, 2652, 2656, 2658, 2695, 2696, 2697, 2700, 2748, 2757, 2799, 2802, 2808, 2850, 2853, 2904, 2907, 2952, 2955, 2958, 3000, 3006, 3055, 3056, 3057, 3060, 3099, 3108, 3150, 3153, 3210, 3213, 3246, 3249, 3250, 3255, 3303, 3304, 3306, 3345, 3351, 3390, 3393, 3456, 3459, 3489, 3492, 3550, 3551, 3555, 3558, 3606, 3609, 3649, 3650, 3654, 3696, 3702, 3747, 3756, 3801, 3807, 3855, 3858, 3895, 3897, 3900, 3903, 3948, 3951, 3954, 3996, 4005, 4047, 4053, 4101, 4104, 4149, 4158, 4194, 4204, 4206, 4251, 4252, 4254, 4257, 4303, 4305, 4308, 4351, 4353, 4356, 4401, 4404, 4449, 4452, 4455, 4500, 4506, 4545, 4548, 4549, 4600, 4605, 4608, 4647, 4650, 4696, 4701, 4755, 4758, 4798, 4800, 4803, 4806, 4848, 4854, 4902, 4911, 4950, 4953, 4995, 4998, 5001, 5055, 5058, 5103, 5106, 5148, 5154, 5199, 5202, 5250, 5253, 5301, 5304, 5349, 5358, 5400, 5401, 5402, 5404, 5406, 5448, 5449, 5450, 5454, 5496, 5506, 5508, 5550, 5553, 5556, 5595, 5598, 5599, 5600, 5601, 5644, 5645, 5646, 5658, 5697, 5698, 5699, 5745, 5754, 5800, 5802, 5808, 5853, 5856, 5901, 5904, 5952, 5958, 5997, 6000, 6045, 6051, 6099, 6108, 6153, 6156, 6198, 6201, 6255, 6256 or 6258 of SEQ ID NO:1, wherein in any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, or 325 variants can be specifically excluded. Certain embodiments are directed to an expression vector configured to express or overexpress an L segment described herein.

The RVFV M-segment can have a nucleotide sequence that is, is at least or is about 90, 91, 92, 93, 94, 95, 96, 97, 98, 99, to 100% identical to the nucleic acid sequence of SEQ ID NO:4. In certain instances the M segment contains 566 single nucleotide polymorphisms throughout the genome. The M segment can also include a deletion of nucleotides corresponding to nucleotide 21 to 384 of SEQ ID NO:2. In certain aspects, the M segment contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, or 167 variant nucleotides at positions 31, 37, 85, 88, 130, 133, 190, 193, 236, 238, 241, 284, 286, 289, 337, 338, 339, 388, 391, 439, 445, 484, 487, 538, 541, 589, 592, 640, 643, 685, 688, 733, 739, 787, 790, 841, 842, 843, 883, 884, 885, 886, 940, 943, 985, 988, 1037, 1039, 1045, 1084, 1090, 1136, 1139, 1140, 1141, 1186, 1189, 1240, 1243, 1285, 1291, 1339, 1342, 1381, 1384, 1393, 1433, 1434, 1435, 1436, 1437, 1438, 1486, 1489, 1534, 1543, 1585, 1588, 1633, 1636, 1639, 1642, 1687, 1693, 1738, 1744, 1783, 1792, 1837, 1843, 1888, 1889, 1891, 1894, 1939, 1942, 1981, 1993, 2032, 2044, 2084, 2089, 2092, 2140, 2143, 2182, 2185, 2236, 2239, 2287, 2288, 2289, 2290, 2293, 2341, 2344, 2386, 2392, 2437, 2400, 2401, 2443, 2491, 2492, 2493, 2494, 2536, 2539, 2587, 2590, 2632, 2633, 2634, 2635, 2686, 2689, 2692, 2737, 2738, 2739, 2740, 2788, 2791, 2831, 2832, 2833, 2836, 2881, 2884, 2938, 2941, 2944, 2986, 2989, 2992, 3034, 3037, 3040, 3079, 3094, 3136, 3139, 3187, 3190, 3193, 3241 or 3244 of SEQ ID NO:4, wherein in any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165 or 166 variants can be specifically excluded. Certain embodiments are directed to an expression vector configured to express or overexpress a M segment described herein.

The RVFV S-segment can have a nucleotide sequence that is, is at least or is about 90, 91, 92, 93, 94, 95, 96, 97, 98, 99, to 100% identical to the nucleic acid sequence of SEQ ID NO:3. In certain instances the S segment contains 73 single nucleotide variants throughout the S segment. In certain aspects, the S segment contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72 or 73 variant nucleotides at positions 50, 53, 98, 104, 147, 149, 152, 191, 194, 243, 245, 246, 248, 293, 296, 350, 353, 392, 393, 449, 452, 500, 503, 542, 546, 547, 548, 597, 599, 602, 647, 650, 690, 698, 749, 752, 901, 904, 952, 955, 1003, 1006, 1048, 1051, 1054, 1102, 1105, 1153, 1156, 1201, 1204, 1207, 1246, 1248, 1252, 1300, 1303, 1348, 1350, 1351, 1396, 1399, 1402, 1447, 1450, 1497, 1498, 1546, 1549, 1600, 1603, 1642 or 1645 of SEQ ID NO:3, wherein in an 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71 or 72 variants can be specifically excluded. Certain embodiments are directed to an expression vector configured to express or overexpress a S segment described herein.

Other embodiments can include a vaccine composition including a vector or a virus as described herein.

Certain embodiments are directed to methods of producing an immune response in a mammal comprising administering one or more of a vector, a virus, or a vaccine as described herein to a mammal, and in particular a human. The virus, vector, or vaccine can be administered by injection, inhalation, or instillation.

Certain embodiments are directed to kits comprising one or more of (a) at least one dose of an attenuated RVFV as described herein.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

Rift Valley Fever Virus (RVFV) is a *Phlebovirus*. It is spread by either touching infected animal blood, breathing in the air around an infected animal being butchered, drinking raw milk from an infected animal, or the bite of infected mosquitoes. Animals such as cows, sheep, goats, and camels may be affected. In these animals it is spread mostly by mosquitoes. The disease is diagnosed by finding antibodies against the virus or the virus itself in the blood. The virus is an enveloped negative single stranded RNA viruses. The virus has an outer lipid envelope with two glycoproteins, Gn and Gc, that are required for cell entry. The virus has an approximately 11.5 kb tripartite genome (L, M, and S segment) composed of single-stranded RNA.

RVFV L segment is a negative-sense RNA that codes a viral polymerase.

RVFV M segment is a negative-sense RNA that encodes two glycoproteins Gn and Gc and nonstructural 78 kD protein and NSm protein.

RVFV S segment is an ambisense RNA encoding nucleoprotein (N) and non-structural protein NSs.

The term "ambisense" refers to a genome or genomic segment(s) having both positive sense and negative sense portions. For example, the S segment of a *Phlebovirus*, such as Rift Valley fever virus, is ambisense, encoding nucleoprotein (NP) in the negative sense and the non-structural protein (NSs) in the positive sense.

The term "attenuated" in the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus.

The term "reverse genetics" refers to the process of introducing mutations (such as deletions, insertions or point mutations) into the genome of an organism or virus in order to determine the phenotypic effect of the mutation. For example, introduction of a mutation in a specific viral gene enables one to determine the function of the gene.

The terms "protein", "peptide", "polypeptide", and "amino acid sequence" are used interchangeably herein to refer to polymers of amino acid residues of any length. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "variant" refers to a polypeptide or nucleic acid differing from a reference nucleic acid or polypeptide, but retaining essential properties thereof. Generally, variants are overall similar, and, in many regions, identical to the reference nucleic acid or polypeptide. A variant can include one or more nucleotide or amino acid substitutions.

As used herein, the terms "antigen" or "immunogen" are used interchangeably to refer to a substance, typically a protein or attenuated virus, which is capable of inducing an immune response in a subject. The term also refers to proteins or viruses that are immunologically active in the sense that once administered to a subject (either directly or by administering to the subject a nucleotide sequence or vector that encodes the protein) is able to evoke an immune response of the humoral and/or cellular type directed against that protein.

As used herein the terms "nucleotide sequences" and "nucleic acid sequences" refer to deoxyribonucleic acid (DNA) or ribonucleic acid (RNA) sequences, including, without limitation, messenger RNA (mRNA), complementary DNA (cDNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" or "heterologous nucleic acid sequence" may be used to refer to "recombinant" nucleotide sequences that may be derived from any of the nucleotide sequences of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

As regards codon optimization, the nucleic acid molecules of the invention have a nucleotide sequence that encodes proteins or polypeptides, and may be designed to employ codons that are used in the genes of the subject in which the protein or polypeptide is to be produced. Many viruses use a large number of rare codons and, by altering these codons to correspond to codons commonly used in the desired subject, enhanced expression of the antigens may be achieved.

For the purposes of the present invention, sequence identity is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin and Altschul, *Proc. Natl. Acad. Sci. USA* 1990; 87: 2264-2268, modified as in Karlin and Altschul, *Proc. Natl. Acad. Sci. USA* 1993; 90: 5873-5877. Another example of a mathematical algorithm used for comparison of sequences is the algorithm of Myers and Miller, *CABIOS* 1988; 4: 11-17. Such an algorithm is incorporated into the ALIGN™ program (version 2.0) which is part of the GCG sequence alignment software package. When utilizing the ALIGN™ program for comparing amino acid sequences, a PAM 120 weight residue table, a gap length penalty of 12, and a gap penalty of 4 may be used. Yet another useful algorithm for identifying regions of local sequence similarity and alignment is the FASTA algorithm as described in Pearson and Lipman, *Proc. Natl. Acad. Sci. USA* 1988; 85: 2444-2448.

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the nucleotides described herein may be used in accordance with the present invention. In certain embodiments, the nucleotide vectors may be used in vitro (such as using cell-free expression systems) and/or in cultured cells grown in vitro in order to produce the encoded RVFV which may then be used for various applications such as in the production of vaccines. For such applications, any vector that allows expression and translation of the nucleotides in vivo, in vitro and/or in cultured cells may be used.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1. Replication kinetics of RVax-1 in culture cells.

FIG. 2. Illustration of vector maps for some examples of the described nucleotides.

(FIG. 3A) Schematic representation of the repetitive units of ribosomal DNA (rDNA). The rDNA operon consists of the 5' external transcribed spacer (ETS), 18S rRNA, internal transcribed spacer (ITS) 1, 5.8S rRNA, ITS2, 28S rRNA, and 3'ETS, and is flanked by the intergenic spacers (IGS). (FIG. 3B) The sequence alignment of precursor rRNA promoter sequences (−234 to −1) of *Homo sapience* (chromosome 21, GenBank #NC_000021.9, position 8388797 . . . 8389034), *Macaca mulatta* (chromosome 20, GenBank #NC_041773.1, position 29808263 . . . 29808496), and Vero cells (GenBank #DI217998.1). The precursor rRNA promoter encodes two functional elements (i) upstream control element (UCE: −156 to −107 relative to the transcription start site+1) and (ii) core control element (CCE: −45 to +18). The CCE determines the species-specific strength of promoter activity. (FIG. 3C) Schematic representation of plasmids encoding full-length antiviral-sense L-, M-, or S-segments of RVFV flanked by the precursor rRNA promoter (−234 to −1) of *Macaca mulatta* and the murine RNA polymerase I terminator.

(FIG. 6A) The genome structure of RVax-1. The RVax-1 encodes a truncation in the M-segment (Δ21-384), which abolishes the expression of the NSm and 78 kD proteins. The RVax-1 encodes 73, 167, or 326 silent mutations in the S-, M-, or L-segment. (FIG. 6B) The replication kinetics of rMP-12 (parental recombinant MP-12 strain) and RVax-1 are shown as plaque-forming unit (PFU)/ml. Vero cells (ATCC CCL-81) were infected with rMP-12 or RVax-1 at MOI 0.01. Both stock viruses were rescued from Vero cells and amplified once in Vero cells. After 1 hr incubation at 37° C. with 5% $CO_2$, cells were washed three times with media. Cells were then incubated at 35° C. with 5% $CO_2$, up to 96 hpi. Virus titers were measured via the plaque assay using Vero cells. (FIG. 6C) Plaques of rMP-12 or RVax-1, which were stained with crystal violet. (FIG. 6D) Western blot analysis of Vero cells infected with rMP-12 or RVax-1 at MOI 5 confirmed a lack of NSm/78 kD protein expression in cells infected with RVax-1. GAPDH was used as a loading control. (FIG. 6E) Cell viability of Vero cells mock-infected or infected with rMP-12 or RVax-1 (MOI 5) was analyzed by MTT assay. Due to a lack of NSm proteins, RVax-1 could induce cell death earlier than parental rMP-12.

FIGS. 7A-C. Genetic stability of RVax-1 in serial passages in Vero cells. The parental rMP-12 or RVax-1 were serially passaged in Vero cells at 35° C. with 5% $CO_2$, to characterize the genetic stability of silent mutations. (FIG. 7A) The MOI at each passage in Vero cells is shown. The range of MOI was 0.004 to 0.037. (FIG. 7B) Northern blot analysis of viral RNA in infected Vero cells at passages 2, 5, and 10. Membranes were reacted with a mixture of RNA probes detecting negative-sense (upper panel) or positive-sense (bottom panel) L-, M-, and S-segment RNA. (FIG. 7C) The RNA-seq analysis of total RNA from Vero cells infected with rMP-12 or RVax-1 was performed with the support of the UTMB NGS core (Director: Steven G. Widen, PhD). None of silent mutations unique to the RVax-1 (n=566) were not changed during 10 passages in Vero cells. The threshold of the variant detection was 1%. The genetic instability of NSs gene ORF was, however, found in both rMP-12 and RVax-1 during their serial passages in Vero cells (data not shown).

(FIG. 8A) Schematic representation of mouse challenge experiment. (FIG. 8B) The levels of viremia at 3 dpv were measured in sera collected from mice vaccinated with rMP-12 or RVax-1. (FIG. 8C) Body weight changes of mock-vaccinated or vaccinated mice are shown for 121 days period. Body weight was normalized to that at Day 0. The means±standard errors of body weight changes per group are shown. (FIG. 8D) The percentage of mouse survival after the challenge with RVFV rZH501 strain. (FIG. 8E) Neutralizing antibody titers of mice vaccinated with rMP-12 or RVax-1 were measured by the Plaque Reduction Neutralizing Antibody Test (PRNT) 80 using MP-12 strain. (FIG. 8F) Anti-RVFV N IgG titers were measured by IgG-ELISA coated with recombinant RVFV N antigen purified with His-tag.

DESCRIPTION

Figure 3A:
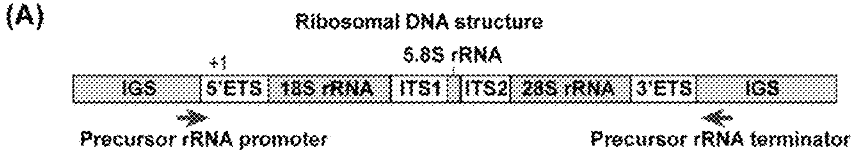
FIGS. 3A-C. The reverse genetics system for Rift Valley fever virus using the precursor rRNA promoter of *Macaca mulatta*.
Figure 3B:
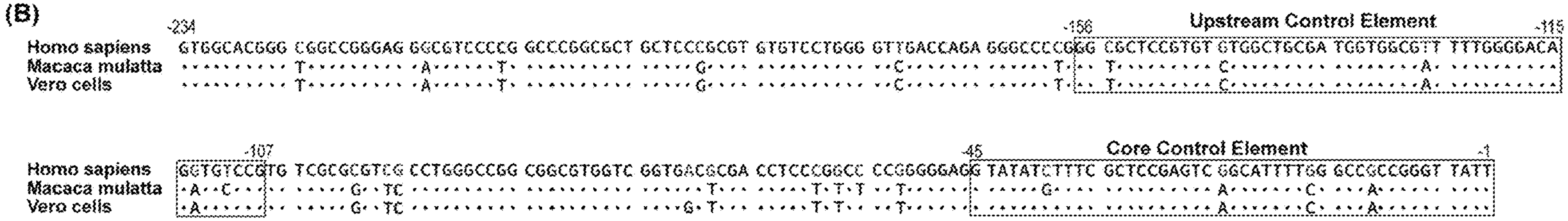
Figure 3C:
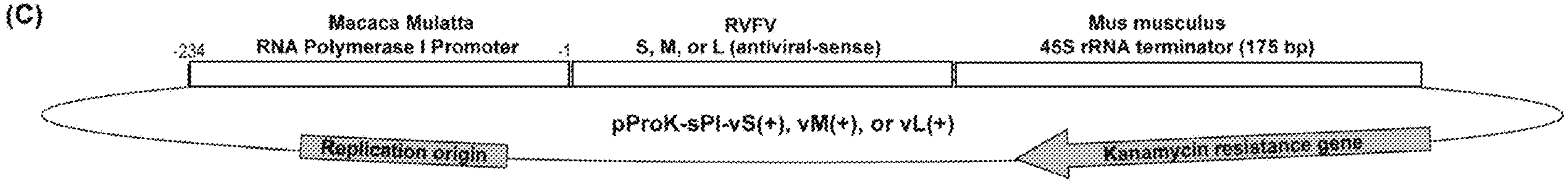
Figure 4A:
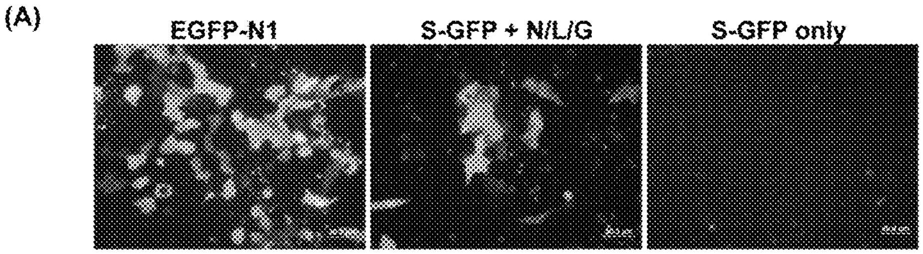
FIGS. 4A-C. Analysis of the RVFV S-segment RNA replication in transfected Vero cells. The RNA replication of the S-GFP genome, in which the NSs gene of the S-segment was replaced with the GFP gene, was evaluated in transfected Vero cells. Although the S-GFP genome encodes the GFP gene, the GFP protein can be expressed only when GFP mRNA is transcribed from the S-GFP, via the support of viral N and L proteins. To evaluate the background transfection efficiency, Vero cells were separately transfected with the EGFP-N1 plasmid, which can constitutively express GFP proteins. The GFP expression from the EGFP-N1 plasmid occurred in up to 20% of cells based on the image analysis (FIG. 4A, left panel), whereas the GFP expression from the S-GFP replication was much less frequent (FIG. 4A, middle panel). Resuspended transfected Vero cells at 72 hours post transfection were subsequently evaluated for the numbers of GFP- and DAPI-positive cells by an automated cell counter. Vero cells expressing EGFP-N1, S-GFP (with N, L, and GnGc proteins), or S-GFP (without N, L, and GnGc proteins) showed GFP signals in 18.3%, 0.47%, or 0% population, respectively (FIG. 4B). Northern blot analysis of total RNA was performed to evaluate the L, M, and S-segment RNA replication in transfected Vero cells (FIG. 4C). Vero cells were mock-transfected or transfected with pProK-sPI-vS(+), pProK-sPI-vM(+), pProK-sPI-vL(+), pCAGGSK-vN, pCAGGSK-vL, or pCAGGSK-vG. Without protein expression plasmids, only the positive-sense S-segment RNA could be visualized, while positive-sense M- or L-segment were too faint to be visualized. Co-expression of N and L proteins with or without GnGc proteins led to accumulations of negative-sense S and M segments, whereas the negative-sense L segment was still not detectable in the analysis.
Figure 4B:
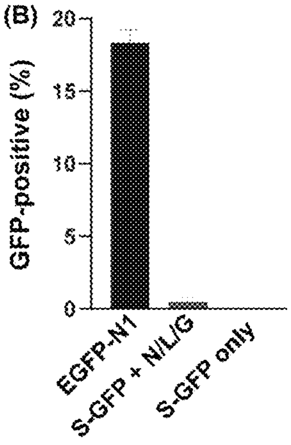
Figure 4C:
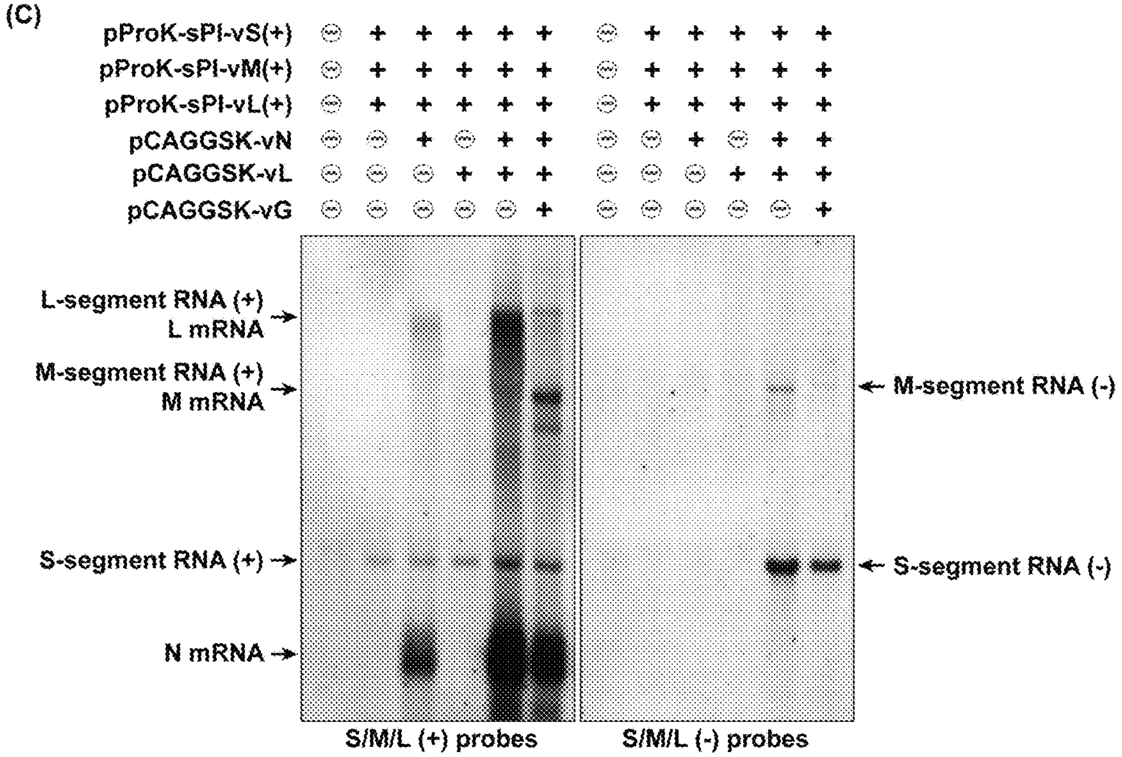
Figure 5:
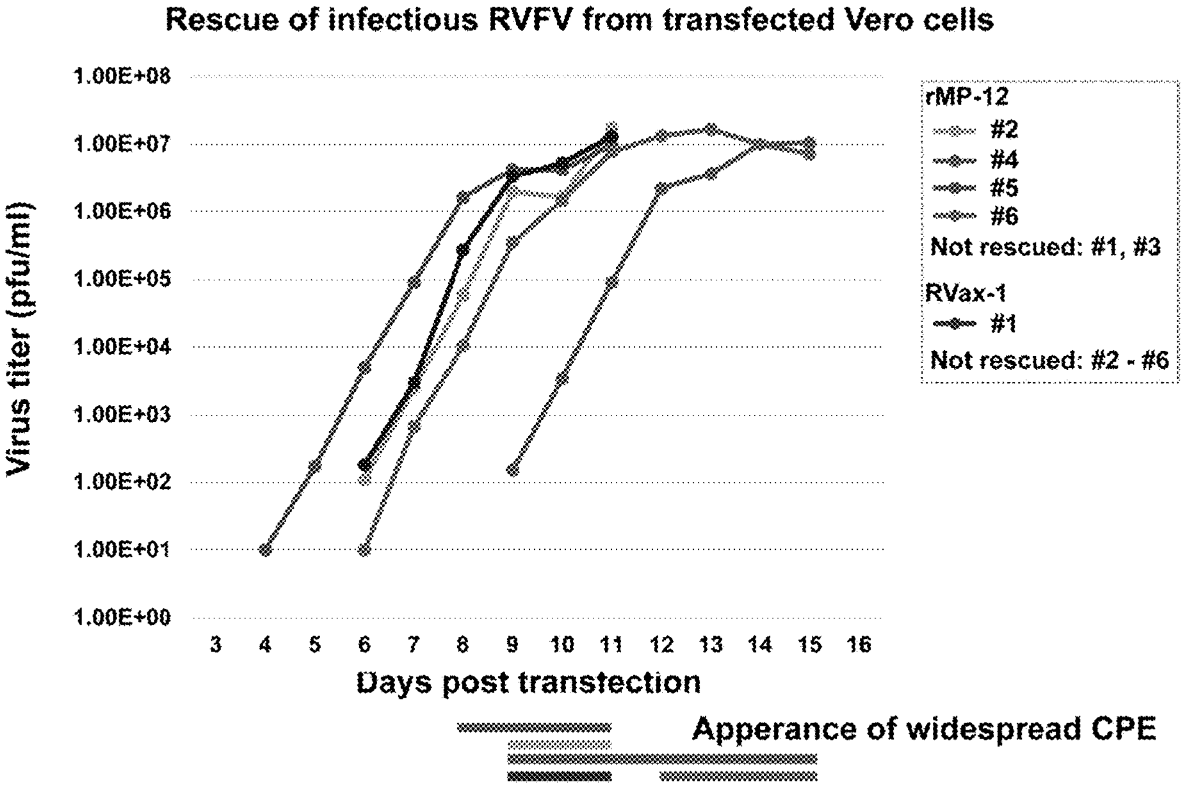
FIG. 5. Rescue of rMP-12 and RVax-1 infectious clones from Vero cells. The recovery of infectious clones of parental recombinant RVFV MP-12 strain (rMP-12) and RVax-1 was performed using Vero cells. Six different wells (#1 to #6) were separately transfected with pProK-sPI-vS(+), pProK-sPI-vM(+), pProK-sPI-vL(+), pCAGGSK-vN, pCAGGSK-vL, and pCAGGSK-vG. Virus titers in culture supernatants and the appearance of cytopathic effect (CPE) in monolayers were analyzed for 16 days post transfection (dpt). Since the 6-well plate became 100% confluent by 72 hpt, cells were re-spread from a well in 6-well plate into a 10 cm dish at 72 hpt. By 7 dpt, all plates showed 10 to 15 small plaque-like foci on monolayers. All foci disappeared gradually in following days in the wells #1 and #3 for rMP-12 or #2, #3, #4, #5, and #6 for RVax-1. The remaining wells #2, #4, #5, and #6 for rMP-12 and #1 for RVax-1 showed a few foci increasing in size, which eventually led to widespread CPE such as rounding or detachment of cells in the monolayers.
Figure 6A:
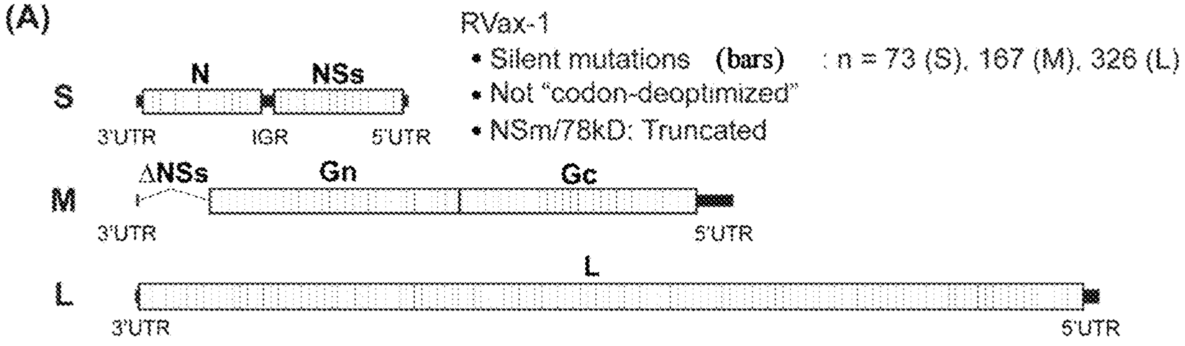
FIGS. 6A-E. Generation and characterization of RVax-1.
Figure 6B:
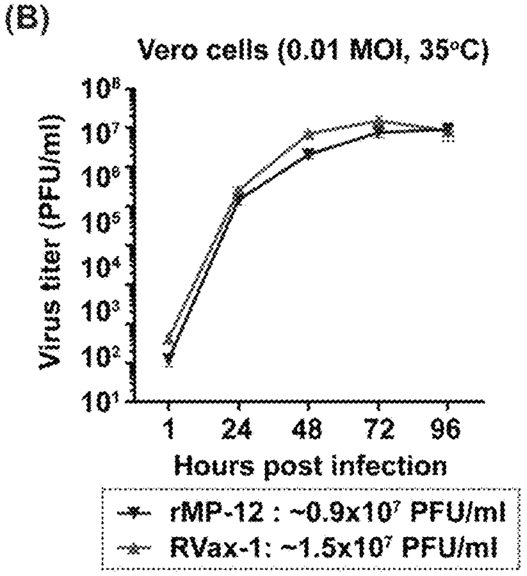
Figure 6C:
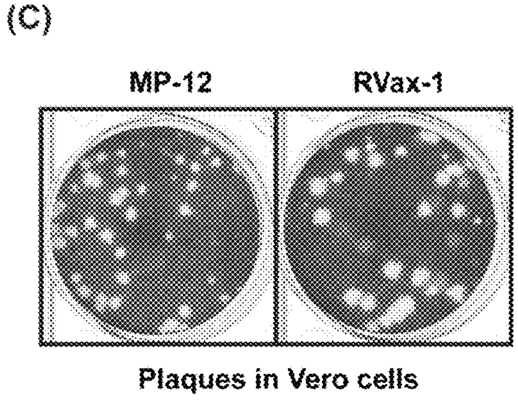
Figure 6D:
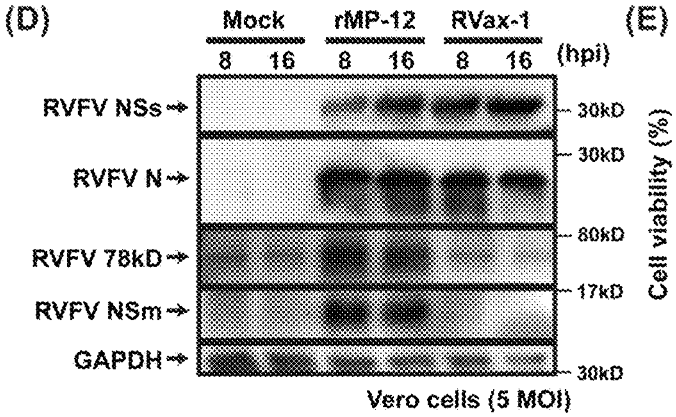
Figure 6E:
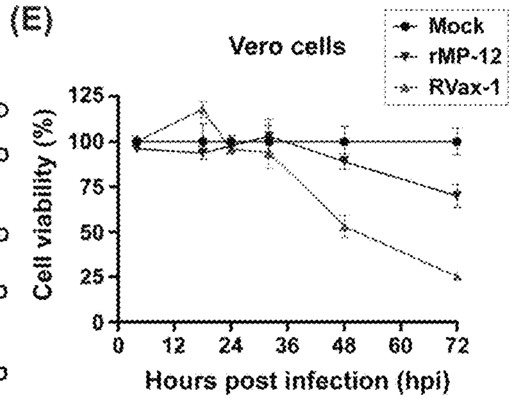
Figure 8A:
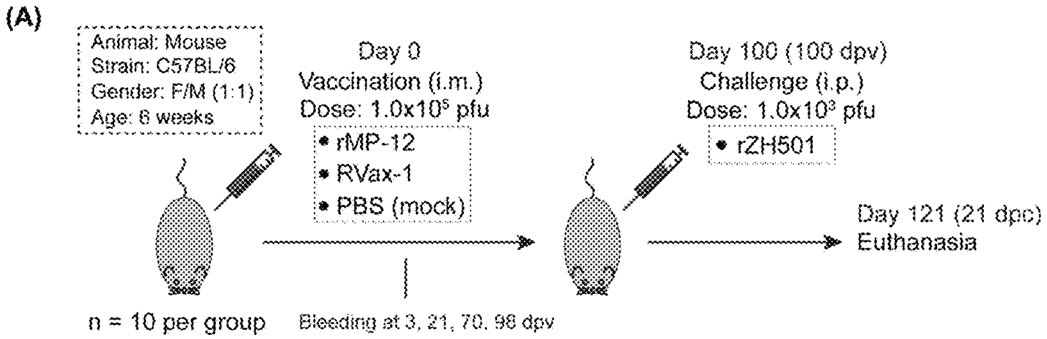
FIGS. 8A-F. Immunogenicity and protective efficacy of RVax-1 in mice. Inbred C57BL/6 mice (6-week-old, M/F=1:1, n=10 per group) were intramuscularly (i.m.) mock-vaccinated with PBS or i.m. vaccinated with $1\times10^5$ PFU dose of rMP-12 (control) or RVax-1. Sera were collected at 3, 21, 70, and 98 days post vaccination (dpv). All mice were then intraperitoneally (i.p.) challenged with $1\times10^3$ PFU dose of pathogenic recombinant RVFV strain ZH501 (rZH501). Mice were monitored for health status and body weight for 21 days post challenge (dpc).
Figure 8B:
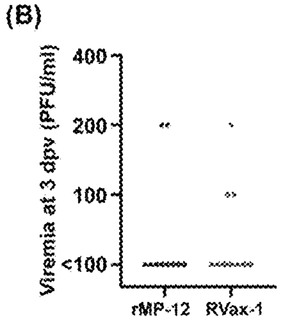
Figure 8C:
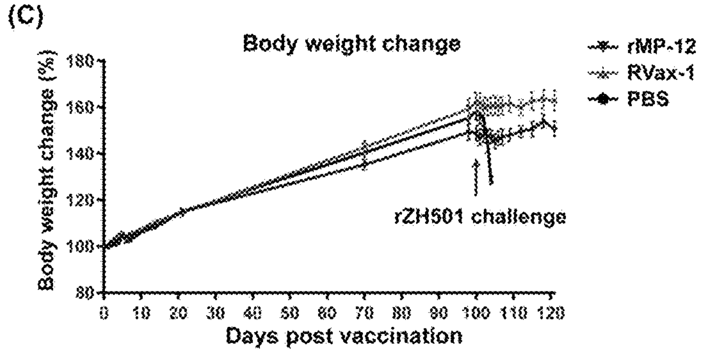
Figure 8D:
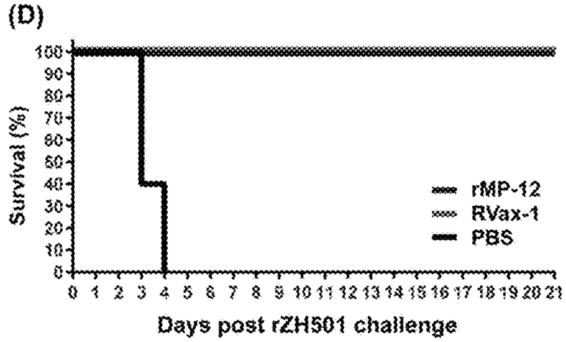
Figure 8E:
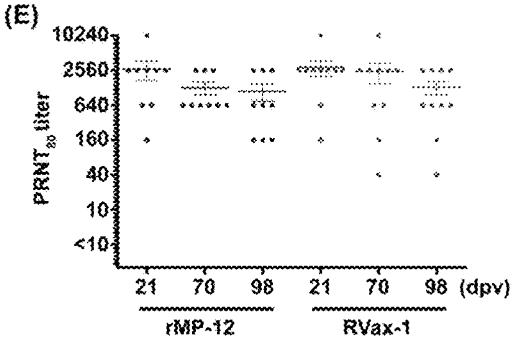
Figure 8F:
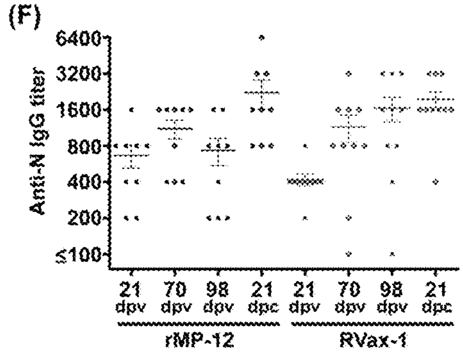

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

I. Rift Valley Fever Virus (RVFV)

Rift Valley Fever Virus (RVFV) is a virus belonging to the family Phenuiviridae and genus *Phlebovirus*. RVF virus has a single-stranded, negative-sense genome composed of three genome segments, S, M and L. The S segment is an ambisense genome segment, meaning it encodes proteins in both the positive-sense and negative-sense orientations. The RVFV genome encodes both structural and non-structural proteins. A "structural" protein is a protein found in the virus particle, whereas a "non-structural" protein is only expressed in a virus-infected cell. RVFV structural proteins include nucleoprotein (NP or N, used interchangeably), two glycoproteins (Gn and Gc) and the viral RNA-dependent RNA polymerase (L protein). Non-structural RVF virus proteins include NSs, NSm and the 78 kD protein. As used herein, a "full-length" RVFV genome segment is one containing no deletions. Full-length genome segments can contain mutations or substitutions, but retain the same length as the wild-type virus. A "complete deletion" of an ORF of a RVFV genome segment means either every nucleotide encoding the ORF is deleted from genome segment, or nucleotides encoding the ORF are deleted such that no proteins are translated from the ORF.

Further provided is a collection of plasmids comprising (i) a plasmid encoding a full-length anti-genomic copy of the L segment of RVF virus; (ii) a plasmid encoding a full-length anti-genomic copy of the M segment of RVF virus, or an anti-genomic copy of the M segment of RVF virus comprising a deletion of the 78 kD/NSm ORF; and (iii) a plasmid encoding an anti-genomic copy of the S segment of RVF virus. In some embodiments, the plasmids further comprise at least one promoter (e.g., RNA polymerase I promoter or a chicken β actin promoter) and one terminator (e.g., RNA polymerase I terminator).

II. Vaccines or Immunogenic Compositions

Provided are immunogenic compositions comprising the recombinant RVFV described herein and a pharmaceutically acceptable carrier. Suitable pharmaceutical carriers are described herein and are well known in the art. The pharmaceutical carrier used depends on a variety of factors, including the route of administration. In one embodiment, the immunogenic composition further comprises an adjuvant. The adjuvant can be any substance that improves the immune response to the recombinant RVFV.

Provided herein are recombinant RVFVs, wherein the genome of the recombinant RVF viruses comprise (i) a full-length L segment (e.g., SEQ ID NO:1); (ii) a full-length M segment (e.g., SEQ ID NO:2) or an M segment comprising a deletion of the NSm open reading frame (ORF) (e.g., SEQ ID NO:4); and (iii) an S segment (SEQ ID NO:3).

Certain embodiments are directed to vaccines or immunogenic compositions comprising one or more of the RVFVs described herein. In one embodiment, the present invention features vaccines or immunogenic compositions comprising a RVFV as described herein.

The RVFV can be administered in vivo, for example where the aim is to produce an immunogenic response in a subject. A "subject" in the context of the present invention may be any animal, such as livestock, or humans. In some embodiments it may be desired to express nucleotides of the invention in a producer cell line.

For such in vivo applications the RVFV can be administered as a component of an immunogenic composition which may comprise the RVFV in admixture with a pharmaceutically acceptable carrier. The immunogenic compositions of the invention are useful to stimulate an immune response against RVFV and may be used as one or more components of a prophylactic or therapeutic vaccine against RVFV for the prevention, amelioration or treatment of Rift Valley Fever.

The compositions of the invention may be injectable suspensions, solutions, sprays, lyophilized powders, syrups, elixirs and the like. Any suitable form of composition may be used. To prepare such a composition, a RVFV having the desired degree of purity is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The immunogenic compositions may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, AlN $a(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, poly IC or poly AU acids, polyarginine with or without CpG (also known in the art as IC31), JuvaVax™, certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand, saponins such as QS21, QS17, and QS7, monophosphoryl lipid A, in particular, 3-de-O-acylated monophosphoryl lipid A (3D-MPL), imiquimod (also known in the art as IQM and commercially available as Aldara®; and the CCR5 inhibitor CMPD167.

Suitable dosages of the immunogens in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal or a subject, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of infection, or evidence of infection, or in advance of any symptom due to infection, especially in high-risk subjects and/or during identified viral breakouts. The prophylactic administration of the immunogenic compositions may serve to provide protective immunity of a subject against RVFV infection or to prevent or attenuate the progression of RVFV in a subject already infected with RVFV. When provided therapeutically, the immunogenic compositions may serve to ameliorate and treat Rift Valley Fever symptoms and are advantageously used as soon after infection as possible, preferably before appearance of any symptoms of Rift Valley Fever but may also be used at (or after) the onset of the disease symptoms.

The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes. Alternatively, delivery routes may be oral, intranasal or by any other suitable route. Delivery may also be accomplished via a mucosal surface such as the anal, vaginal or oral mucosa. Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one, two, three, or four. The methods of inducing an immune response may also include administration of an adjuvant with the immunogens. In some instances, annual, biannual or other long interval (5-10 years) booster immunization may supplement the initial immunization protocol.

Methods may also include a variety of prime-boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. One useful prime-boost regimen provides for two priming immunizations, four weeks apart, followed by two boosting immunizations at 4 and 8 weeks after the last priming immunization.

Certain embodiments of the invention provide methods of inducing an immune response against RVFV in a subject by administering an immunogenic composition described herein one or more times to a subject to induce a specific immune response in the subject. Such immunizations may be repeated multiple times at time intervals of at least 2, 4 or 6 weeks (or more) in accordance with a desired immunization regime.

The immunogenic compositions of the invention may be administered alone, or may be co-administered, or sequentially administered, with other immunogens and/or immunogenic compositions, e.g., with "other" immunological, antigenic, vaccine, or therapeutic compositions thereby providing multivalent or "cocktail" or combination compositions of the invention and methods of employing them. Again, the ingredients and manner (sequential or co-administration) of administration, as well as dosages may be determined taking into consideration such factors as the age, sex, weight, species and condition of the particular subject, and the route of administration.

It is to be understood and expected that variations in the principles of invention as described above may be made by one skilled in the art and it is intended that such modifications, changes, and substitutions are to be included within the scope of the present invention. The dose of the vaccine may vary according to factors such as the disease state, age, sex, and weight of the individual, and the ability of antibody to elicit a desired response in the individual. Dosage regime may be adjusted to provide the optimum therapeutic response. The dose of the vaccine may also be varied to provide optimum preventative dose response depending upon the circumstances.

Further provided is a method of immunizing a subject against RVF virus infection, comprising administering to the subject an immunogenic composition disclosed herein. In one embodiment, the subject is livestock. Livestock includes, but is not limited to sheep, goats, camels, and cattle. In another embodiment, the subject is a human. In one example, the immunogenic composition is administered in a single dose. In another embodiment, the immunogenic composition is administered in multiple doses, such as two, three or four doses. When administered in multiple doses, the time period between doses can vary. In some cases, the time period is days, weeks or months. The immunogenic composition can be administered using any suitable route of administration. Generally, the recombinant RVFV are administered parenterally, such as intramuscularly, intravenously or subcutaneously.

III. Use of Recombinant RVF Viruses

Recombinant RVFV generated using the reverse genetics system described herein can be used for both research and therapeutic purposes. Such recombinant RVFV can be used as vaccines to prevent infection of livestock and humans with wild-type RVF virus. The recombinant RVFV described herein can also be used as live-virus research tools, particularly those viruses that incorporate reporter genes, for instance a fluorescent protein such as GFP. For example, these viruses can be used for high-throughput screening of antiviral compounds in vitro.

The enhanced safety, attenuation, and reduced possibility of virulent RVFV (via either RVF virus polymerase nucleotide substitution or gene segment reassortment with field-strains) while maintaining overall vaccine efficacy. A high level of protective immunity can be induced by a single dose of the rRVF viruses disclosed herein.

IV. Kits

Certain embodiments are directed to for example for preventing or treating an infection. For example, a kit may comprise one or more pharmaceutical compositions or vaccines as described above and optionally instructions for their use. In still other embodiments, the invention provides kits comprising one or more pharmaceutical compositions or vaccines and one or more devices for accomplishing administration of such compositions.

Kit components may be packaged for either manual or partially or wholly automated practice of the methods described herein. In other embodiments involving kits, it is contemplated that a kit includes compositions described herein, and optionally instructions for their use. Such kits may have a variety of uses, including, for example, imaging, diagnosis, therapy, and other applications.

The invention claimed is:

1. A composition comprising a Rift Valley Fever Virus (RVFV) comprising:

(i) an L segment, (ii) an M segment having a nucleic acid sequence of SEQ ID NO:4, and (iii) an S segment.

2. The composition of claim 1, wherein the L segment has at least 90% identity to the nucleic acid sequence of SEQ ID NO:1.

3. The composition of claim 1, wherein the S segment has at least 90% identity to the nucleic acid sequence of SEQ ID NO:3.

4. The composition of claim 1, wherein the L segment has 100% identity to the nucleic acid sequence of SEQ ID NO:1.

5. The composition of claim 1, wherein the S segment has 100% identity to the nucleic acid sequence of SEQ ID NO:3.

6. An immunogenic composition comprising the composition of claim 1 and a pharmaceutically acceptable carrier.

7. A host cell expressing the L segment, M segment, and S segment of claim 1.

8. A method of producing an immune response in a mammal comprising administering the RVFV virus of claim 1 to a mammal.

9. The method of claim 8, wherein the mammal is a human.

10. The method of claim 8, wherein the vector is administered by injection, inhalation, or instillation.

11. The method of claim 10, wherein the vector is administered by intramuscular injection.

12. The method of claim 8, wherein the administering confers immunity to Rift Valley Fever caused by Phenuiviridae *Phlebovirus.*

13. A method of producing an immune response in a mammal comprising administering the immunogenic composition of claim 6 to a mammal.

14. A method of producing the RVFV of claim 1 comprising:

(a) culturing a non-rodent cell comprising:

(i) cDNA of full-length RVFV L segment, (ii) cDNA of full-length RVFV M segment or RVFV M segment lacking 78 kD/NSm ORF, (iii) cDNA of full-length RVFV S segment, (iv) cDNA of RVFV N open reading frame (ORF), (v) cDNA of RVFV M ORF, and (vi) cDNA of RVFV L ORF, (b) isolating RVFV produced by culturing the non-rodent cell.

15. The method of claim 14, wherein cDNAs (i), (ii), and (iii) are, independently, immediately downstream of human or rhesus monkey RNA polymerase I promoter and upstream of mouse RNA polymerase I terminator.

16. The method of claim 14 wherein expression of ORFs (iv), (v) and (vi) are independently controlled by a chicken β-actin promoter.

* * * * *

SEQUENCE LISTING

<160> NUMBER OF SEQ ID NOS: 4

<210> SEQ ID NO 1
<211> LENGTH: 6404
<212> TYPE: DNA
<213> ORGANISM: Rift Valley fever virus

<400> SEQUENCE: 1
acacaaaggc gcccaatcat ggattctata ttatcaaaac agctggtgga caaaactggt 60
tttgttagag tgccaatcaa gcattttgac tgtacaatgc taacacttgc acttccaaca 120
tttgatgttt ccaagatggt agatagaata accattgact tcaatctgga tgatatacaa 180
ggagcatctg aaataggctc cactcttcta ccctccatgt cgatagatgt ggaagatatg 240
gccaattttg ttcatgactt cacctttggc cacttagctg acaagactga ccgcctgctc 300
atgcgtgagt ttcccatgat gaatgacggg tttgatcatt tgtccccaga tatgatcatt 360
aaaactacat ctggcatgta caacatcgtt gagttcacca ccttcagagg agatgaaaga 420
ggtgcattcc aggctgccat gactaaactt gccaagtatg aggttccttg tgagaacaga 480
tctcagggca ggactgtggt cctttacgtt gttagtgctt atcggcatgg tgcatggtct 540
aatctggagc tagaagattc tgaagcagag gagatggttt ataggtacag acttgctctc 600
tctgtgatgg atgagctaag gaccttgttc ccagaactgt catccactga tgaagaacta 660
gggaagactg agagagagtt gctagccatg gtttccagca tccaaataaa ttggtcagtc 720
acagaatctg tgtttccacc cttctccagg gaaatgtttg acaggtttag atcctcccct 780
cccgattcag agtatatcac cagaattgtg agcagatgcc taataaattc tcaagagaaa 840
ctcatcaatt ccagcttctt tgctgaaggg aatgataagg ctctgagatt ttcaaaaaac 900
gccgaggagt gttccttggc agtagagaga gccttaaatc agtaccgggc agaggacaac 960
cttagggacc tcaatgacca caagtcaact attcaacttc ctccctggct gtcctatcat 1020
gatgtcgatg gcaaagatct gtgcccccctg cagggactag atgtgagagg ggaccatccc 1080
atgtgcaact tgtggagaga ggtggtcacc tctgcaaacc tagaggagat tgagaggatg 1140
cacgatgatg ctgctgcaga acttgagttt gccctttcgg gagtaaagga caggccagat 1200
gaaaggaaca gataccatag agtccaccta aatatgggct cagatgattc tgtctacatt 1260
gctgctttag gagttaatgg aaagaagcat aaagcagaca ctttggtcca acaaatgaga 1320
gacaggagta aacagccttt cagcccggac cacgatgtgg atcacatatc tgaatttctc 1380
tctgcatgct ctagtgatct ttgggcaaca gatgaggacc tgtacagccc tctctcttgt 1440

-continued

```
gataaagagc tgaggcttgc agcccagagg attcatcagc catccttgtc agaaaggggc   1500
tttaatgaga tcataacaga gcactacaaa ttcatgggaa gtagaattgg ctcatggtgc   1560
caaatggtca gcttgatagg agctgagcta tcagcctctg tgaaacaaca tgtcaagcct   1620
aactactttg tgattaaacg actactagga tctggcattt tcttgctaat caagcccact   1680
tccagcaaaa gccatatatt tgtttccttt gcaattaagc gctcttgctg ggcctttgat   1740
ctctccactt cccgcgtctt caagccctac atagatgctg gggatctgct ggtcactgat   1800
tttgtttctt ataagctaag caagcttacc aacctctgca agtgcgttag cctcatggag   1860
tcctccttct cattctgggc agaagcattt ggaattcctt cctggaactt tgttggtgac   1920
ttgttcaggt cttcagactc tgctgccatg gatgcttcat acatgggcaa actttcttta   1980
ttaacccttt tggaagacaa agctgccact gaagagttac agactattgc aagatatata   2040
atcatggaag gttttgtctc gcccccagaa atcccaaaac ctcacaagat gacctctaag   2100
ttcccaaagg ttctcaggtc agagctgcaa gtttacttat taaactgtct ttgcagaact   2160
atccagagaa tagcaggtga gcccttcatt cttaagaaga aagatggatc tatatcctgg   2220
ggtggcatgt tcaatccttt ttcagggaga cctctccttg atatgcaacc actcatcagc   2280
tgttgttaca atggctactt caaaaataaa gaagaagaga ctgagccttc gtccctttct   2340
gggatgtata agaagattat agaacttgag caccttagac cacagtcaga tgccttcttg   2400
ggatataaag atccagaact tcccagaatg catgagttca gtgtttctta cctcaaggag   2460
gcttgcaatc atgctaagct agtcttgagg agcctctatg gacaaaactt catggagcag   2520
atagacaacc agattattcg agagctctct ggcctcactc tagaaaggtt ggccacactt   2580
aaggccacaa gcaacttcaa tgagaactgg tatgtctata aggatgtagc agacaaaaac   2640
tacacaaggg acaaactttt agtgaagatg tcaaaatatg cctctgaggg aaagtctctt   2700
gctatccaga agtttgagga ttgtatgagg cagatagagt cacaaggttg catgcacatt   2760
tgtttgttta agaaacaaca gcatggaggt ctgagagaaa tttatgtcat gggtgcagag   2820
gaaagaattg ttcaatcggt ggtggagacc attgccaggt ccatagggaa gttctttgct   2880
tctgataccc tctgtaaccc cccaaacaaa gtgaaaattc ctgaaacaca tggcatcagg   2940
gcccggaagc agtgcaaagg gcctgtgtgg acttgtgcaa catcagatga tgcaaggaaa   3000
tggaatcaag gccattttgt tacaaagttt gccctcatgc tgtgtgagtt caccagcccc   3060
aaatggtggc cgctgatcat taggggatgc tcaatgttca ccaagaagag gatgatgatg   3120
aatttgaatt atcttaagat cctggatggc caccgggagc ttgatattag agatgacttt   3180
gtgatggatc tcttcaaggc ttatcatggt gaagcagaag ttccatgggc ctttaaaggc   3240
aaaacttacc tggagaccac aacagggatg atgcagggaa tactgcatta tacttcctca   3300
cttctgcaca ccattcacca agaatacatc cggtccttgt ccttcaagat cttcaacctg   3360
aaggttgctc ctgagatgag caagagcctt gtctgtgaca tgatgcaagg atcagatgat   3420
agtagtatgc taatcagctt cccagctgat gatgaaaaag ttcttaccag atgcaaagtg   3480
gccgcagcca tctgcttccg catgaagaag gagctgggag tgtaccttgc catttacccc   3540
tcagagaaga gcactgccaa cacagatttt gtgatggagt acaattctga attttatttc   3600
cacactcaac atgttagacc aacgatcagg tggattgcag cttgttgctc cctcccagaa   3660
gtggaaacac tagtagcccg ccaggaagag gcctccaacc tcatgacttc agttactgag   3720
ggaggtgggt cattctcctt agctgccata attcaacaag ctcagtgtac tctccattac   3780
```

-continued atgctgatgg gcatgggagt ctctgaacta ttcttagagt ataagaaggc agtgctgaag 3840
tggaatgacc ctggtcttgg tttcttcctg cttgacaatc cttatgcgtg cggacttggt 3900
ggcttcagat ttaatctctt caaagctatc accagaactg atttgcaaaa actttatgct 3960
ttcttcatga agaaggtcaa gggctcagct gctagagact gggctgatga agatgtcacc 4020
atcccagaaa cgtgtagcgt gagccctggt ggagctctaa ttcttagctc ctctctaaag 4080
tggggatcta ggaagaagtt ccaaaaattg agagaccgtt tgaacatacc agagaactgg 4140
attgaactta taaatgaaaa tccagaggtg ctctatcggg ctcccagaac aggtccagaa 4200
atacttttgc gcattgcaga gaaagtccat agcccaggtg ttgtgtcatc tctctcctct 4260
ggcaatgcag tttgtaaagt catggcctca gctgtatact tcctttctgc aacaattttt 4320
gaggacactg gacgtcctga gttcaacttc ctagaagatt ctaagtatag cttgctacaa 4380
aagatggctg catattctgg tttccatggt ttcaatgata tggagccaga agatatatta 4440
ttcttatttc ctaacattga ggaattagaa tcactggatt ctatagttta caacaagggt 4500
gaaattgaca tcatcccaag agtcaacatc agggatgcaa cccagactcg ggtcactatc 4560
tttaatgagc agaagaccct ccggacatct ccagagaagc tggtctctga caagtggttt 4620
gggactcaga agagtaggat aggcaagacc accttcctgg ctgaatggga aaagctaaag 4680
aaaattgtaa agtggctgga ggacactcca gaagcaactc tagctcacac cccactgaat 4740
aaccatattc aagtcagaaa tttctttgct agaatggaaa gcaagcctag aacagtccgc 4800
atcactggag ctccagtaaa gaagaggtca ggggttagta agatagccat ggtgatccgt 4860
gacaatttct cccggatggg ccatcttcga ggtgtagaag atcttgctgg tttcactcgt 4920
agtgtgtcag ctgaaattct caagcacttc ctgttctgta tactacaagg tccatacagt 4980
gagagctata agcttcaact tatctacaga gtcctaagct cagtgtcaaa cgttgagata 5040
aaggaatcag atggcaaaac aaaaaccaac ttgattggaa tccttcagag atttctagat 5100
ggagaccacg ttgtccccat aattgaagag atgggagccg gaacagttgg tggtttcatc 5160
aagagacaac aatctaaagt tgtgcagaac aaagtggtgt actatggggt tgggatttgg 5220
agaggcttca tggatggata tcaggtccac ctggagatag aaaatgacat aggacagccc 5280
ccaaggctta ggaatgtcac cacaaactgt cagagcagcc catgggacct gagtattcca 5340
ataaggcagt gggcagagga catgggggtc acaaacaacc aggattattc ctctaaatca 5400
tcccgcgggg ccagatattg gatgcattca ttcaggatgc aaggaccatc caaaccattt 5460
ggatgcccag tttatattat taagggtgat atgtctgatg tcatccgcct gagaaaggag 5520
gaggtggaga tgaaagtacg gggctctaca cttaatttgt acaccaagca ccattctcat 5580
caggacctac acatcctgag ctacactgca tcagacaatg atctcagtcc aggcattttc 5640
aagagcatat cagatgaagg ggtggctcaa gccctgcaat tatttgagag ggagccctcc 5700
aactgctggg tgagatgtga gtctgtagcc ccaaaattta tatctgccat cctggagata 5760
tgtgagggga agagacagat aaagggaatt aacagaaccc ggctctctga gattgtgaga 5820
atttgttctg aatcttccct aagatcaaaa gttggctcta tgttctcatt tgtcgccaat 5880
gtcgaggagg cccatgatgt ggactatgat gcgttaatgg atctaatgat agaggatgcc 5940
aagaacaatg ccttcagcca tgttgttgac tgcatagagt tggatgttag tggcccctat 6000
gagatggagt cttttgatac atctgatgtc aatctctttg ggcctgccca ctacaaggac 6060
atcagttcat tatctatgat tgctcatccc ttaatggaca agtttgtgga ttatgctatt 6120
tctaagatgg ggagagcctc agttaggaaa gtccttgaaa caggtcggtg ctccagcaaa 6180

-continued gactatgatt tatcaaaagt gctcttcaga actctacaga gaccagaaga aagcattagg 6240
atagatgatc tggagctcta tgaggagaca gatgtggcgg atgacatgct aggctaagac 6300
cagtaagcaa agtcaggctt agatttaggg atactatgct agtattggaa tccatgtggg 6360
ttctgatact agcatagtgc tacaatattg ggcggtcttt gtgt 6404

<210> SEQ ID NO 2
<211> LENGTH: 3885
<212> TYPE: DNA
<213> ORGANISM: Rift Valley fever virus

<400> SEQUENCE: 2
acacaaagac ggtgcattaa atgtatgttt tattaacaat tctaaccagc gtcctggtgt 60
gtgaagcgat tattagagtg tctctaagct ccacacggga ggagacctgc tttggtgact 120
ccactaaccc agagatgatt gaaggagcct gggactcact cagagaggag gagatgccgg 180
aggagctctc ctgctccata tcaggcataa gagaggttaa gacctcaagc caggagttat 240
accgggcttt aaaagccatc attgctgctg atggcttgaa caacatcacc tgccatggaa 300
aagatcctga ggacaagatt tccctcataa agggtcctcc tcacaaaaag agagttggga 360
tagttcggtg tgagagacga agagatgcta agcagatagg aagagaaacc atggcaggga 420
ttgcaatgac agtccttcca gccttagctg tctttgcttt ggcacctgtt gtttttgctg 480
aagaccccca tctgaggaac agaccaggga aggggcacaa ctacattgac gggatgactc 540
aggaggatgc cacttgtaaa cctgtgacat atgctggggc atgtagcagt tttgatgtcc 600
tcctggaaaa gggaaaattt cccctttcc agtcgtatgc tcatcatcgc acactactag 660
aggcagttca cgacaccatc attgcaaagg ctgatccacc atcctgtgac cttctgagtg 720
ctcatgggaa cccctgcatg aaagagaaac tggtcatgaa gacacactgt ccaaatgact 780
accagtcagc tcatcacctc aataatgatg ggaaaatggc ttcagtcaag tgccctccta 840
agtatgaact tactgaagac tgcaactttt gtaggcagat gacaggtgct agcctgaaga 900
aaggctctta tcctctccaa gacttgtttt gtcagtcaag tgaggatgat ggctccaaat 960
taaaaacaaa aatgaaaggg gtctgcgaag tgggggttca agctcttaaa aagtgtgatg 1020
gccaactcag cactgcacat gaggttgttc cttttgcagt gtttaagaac tcaaagaagg 1080
tttatcttga taagctggac ctgaagactg aggagaatct gctaccagac tcatttgtct 1140
gtttcgagca caaaggacag tacaaaggaa caatggactc tggtcagact aagagggagc 1200
tcaagtcctt tgatatctct cagtgcccca agattggagg acatggatca aagaagtgca 1260
ctggggacgc agcattttgc tctgcttatg agtgcactgc tcaatatgcc aatgcctatt 1320
gttcacatgc taatgggtca gggattgttc aaatacaagt atcaggggtc tggaagaagc 1380
ctttatgtgt agggtatgag cgcgtggtgg tgaagagaga actctctgcc aagcccatcc 1440
agagagtgga gccgtgcaca acttgtataa ccaaatgtga gcctcatgga ttggttgtca 1500
gaagcacagg gttcaagata tcatcagcag ttgcttgtgc tagcggagtc tgtgtcacag 1560
gatcgcagag tccttccacc gagattacac tcaagtatcc aggtatttcc cagtcttctg 1620
ggggggacat aggggttcac atggcacatg atgaccagtc agttagctcc aaaatagtag 1680
ctcactgccc tccccaggac ccctgtttag tgcatgactg catagtgtgt gctcatggcc 1740
tgatcaacta ccagtgccac actgctctca gtgcctttgt tgttgtgttt gtattctcca 1800
gcattgcaat aatttgttta gctattcttt atagggtgct taagtgcctc aaaattgccc 1860

-continued

```
caaggaaagt tctgaatcca ctaatgtgga tcacagcttt catcaggtgg atatataaga   1920

agatggttgc cagagtggca gacaacatca accaagtgaa cagggaaata ggatggatgg   1980

aaggaggtca gttggtcctg ggaaatcctg cccctattcc tcgtcatgcc ccaatcccac   2040

gttatagcac ctacctcatg ttattattga ttgtctcata tgcatcagca tgttcagaac   2100

tcattcaagc aagctccaga atcaccactt gctctacaga gggtgtcaac accaaatgta   2160

gactgtctgg cacagcattg atcagagcag ggtcagttgg agcagaagct tgtttgatgt   2220

tgaagggggt caaggaagat caaaccaagt ttcttaaatt aaaaactgtc tcaagtgagc   2280

tatcatgcag ggagggccag agctactgga ctgggtcctt tagccctaaa tgtttgagct   2340

caagaagatg ccacctggtc ggggaatgcc atgtgaatag gtgtctgtct tggagagaca   2400

atgaaacatc agcagagttt tcatttgttg gggaaagcac gaccatgaga gaaaacaagt   2460

gttttgagca atgtggagga tgggggtgtg ggtgtttcaa tgttaatcca tcttgcttat   2520

ttgtgcacac gtatctgcag tcagtgagga aagaggccct tagagttttt aactgtatcg   2580

actgggtgca taaactcacc ctggagatca cagactttga tggctctgtt tcaacaatag   2640

acttgggagc cagctccagc cgtttcacaa actggggttc agttagcctc tcactggacg   2700

cagaaggaat ttcaggctca aatagctttt ctttcattga gagcccagga aaaggatatg   2760

caattgttga tgagccattc tcagaaattc ctcggcaagg atttcttggg gagatcaggt   2820

gcaattcaga gtcctcagtc ctgagtgctc atgagagctg ccttagggca ccaaacctta   2880

tctcatacaa gcccatgatt gaccaattgg agtgcacaac aaatctgatt gatccctttg   2940

ttgtctttga aagaggttct ctgccacaga caaggaatga caaaaccttt gcagccagca   3000

aaggaaatag aggtgttcaa gctttctcta agggctctgt acaagctgac ctcaccctga   3060

tgtttgacaa ttttgaggtg gactttgtgg gagcagccgt cagctgtgat gccgccttct   3120

taaatttgac aggttgctat tcttgcaatg ctggtgccag ggtctgcctg tctatcacat   3180

ccacaggaac tggaagcctt tctgcccaca ataaggatgg gtctctgcat atagtccttc   3240

catctgaaaa tggaacaaaa gaccagtgtc agatactaca cttcactgtg cctgaagtag   3300

aagaagaatt tatgtactct tgtgatggag atgagcggcc tctgttggtc aaaggcaccc   3360

tgatagccat tgatccattt gatgataggc gggaagctgg aggtgaatca acagttgtga   3420

atccaaaatc tggatcttgg aacttctttg actggttctc tggactcatg agttggtttg   3480

gagggcctct taaaactatt cttctcattt gcctgtatgt tgcattatca attgggctct   3540

ttttcctcct catctacctt ggaggaacag gcctctctaa aatgtggctt gctgccacta   3600

agaaagcttc atagatcagt gcgtgtaaaa gcaatatgtt gaagtaagta gacataagct   3660

aacctaatta tgtaagtatt gtacagatag gtcaaattat tggaatatcc aagcttagaa   3720

acttatgcaa taatacttta gatgtaagct tagttgtaat ttggggtggt ggggtgaggc   3780

agcagcagtc tcaagtgctt gtgaatattc tagttggcgt aatcgtcttt tgccagatta   3840

gctgggaatt aaactaactc tttgaagttg caccggtctt tgtgt                   3885
```

<210> SEQ ID NO 3
<211> LENGTH: 1690
<212> TYPE: DNA
<213> ORGANISM: Rift Valley fever virus

<400> SEQUENCE: 3

```
acacaaagct ccctagagat acaaacacta ttacaataat ggacaactac caggagcttg     60

cgatccagtt tgctgctcaa gcagtggacc gcaatgaaat tgagcagtgg gtccgagagt    120
```

```
ttgcttatca agggtttgat gcccgtcggg tcatcgaact cttaaagcag tatggtgggg    180
ctgactggga aaaagatgcc aagaaaatga ttgttctggc tctaactcgt ggcaacaagc    240
cccgccgcat gatgatgaaa atgtcgaaag aaggcaaagc aactgtggag gcccttatca    300
acaagtataa gctaaaggaa gggaatcctt cccgggatga gttgactctt tcccgagttg    360
ctgccgcctt ggctggctgg acatgccagg ccctggtcgt cttgagtgag tggcttcctg    420
tcactgggac taccatggac ggcctatctc cagcataccc gaggcatatg atgcacccca    480
gctttgctgg catggtggac ccatctctac caggagacta tctaagggca atattagatg    540
cccacagcct gtatctgctg cagttctccc gggtcatcaa cccaaacctc cgaggtcgca    600
ccaaagagga ggttgctgca acgttcacgc agccaatgaa tgcagctgtt aatagcaact    660
ttataagcca tgagaagagg agagaattcc tgaaagcttt tggacttgtg gattccaatg    720
ggaagccgtc agctgctgtc atggcagctg cccaggctta caagacagca gcctaagtgg    780
ctgcccaggg ggttgggggg aaggggagtt ggggttacgg tcgggattag gggtggggg     840
gtggggcagc cttaacctct aatcaacctc aacaaatcca tcatcatcac tctcctcctc    900
agactccatc tcaacatctg ggattggagg aataactgga atccagttgt tccttcccat    960
catgctggga agtgatgagc gcagcatcag gctctcctcc atcaggacaa tgagggctga   1020
gtttggaact acagcattag aaatgtcttc cttggctgct tgcagaagcc gaacgcactg   1080
tacgtgagca acctcataca tcaggtcaaa gcctggcaac aggcacaggt caatccctct   1140
gaggatggcc tctgtagcta tcatcctgtg taagccagca aaggagtcct ctagatcatt   1200
tgtaattttg caactcctca ttgctagagt ggcaatctga tccctccgaa tatcatcatt   1260
cctatgcact ctagtagagc ttaggtcgaa gaaagccaga gatggttctc caagaggcca   1320
ggatatggct tctttcagat tggggaagcg ggtgaaatca ctaagagtca tatggcctat   1380
tagatcaata agtctttgga agggcttcgc tggtggaggt gcaacgtttg atgcaaagtc   1440
tccaagacca actcggtatg ggaattctcc gacattgtag aagtcagaga atcgcagccg   1500
aacctcgtga ctaggacgat ggtgcatgag aaagacacaa caggggccca ccatagaata   1560
aggtatcctg ggaggaccat ctcctctaaa gtactccaca gagacaacac gacgaccact   1620
ctgcaaatca acagatatca ctgggaagta atccatgata tacttgataa gcactagggg   1680
gtctttgtgt                                                          1690
```

```
<210> SEQ ID NO 4
<211> LENGTH: 3521
<212> TYPE: DNA
<213> ORGANISM: Artificial Sequence
<220> FEATURE:
<223> OTHER INFORMATION: synthetic nucleic acid

<400> SEQUENCE: 4

acacaaagac ggtgcattga attctaagca gataggaaga gaaaccatgg cagggattgc     60
aatgacagtc cttccagcct tagctgtctt tgctttggca cctgttgttt ttgctgaaga    120
cccccatctg aggaacagac cagggaaggg gcacaactac attgacggga tgactcagga    180
ggatgccact tgtaaacctg tgacatatgc tggggcatgt agcagttttg atgtcctcct    240
ggaaaaggga aaatttcccc ttttccagtc gtatgctcat catcgcacac tactagaggc    300
agttcacgac accatcattg caaaggctga tccaccatcc tgtgaccttc tgagtgctca    360
tgggaacccc tgcatgaaag agaaactggt catgaagaca cactgtccaa atgactacca    420
```

-continued

```
gtcagctcat cacctcaata atgatgggaa aatggcttca gtcaagtgcc ctcctaagta    480
tgaacttact gaagactgca acttttgtag gcagatgaca ggtgctagcc tgaagaaagg    540
ctcttatcct ctccaagact tgttttgtca gtcaagtgag gatgatggct ccaaattaaa    600
aacaaaaatg aaaggggtct gcgaagtggg ggttcaagct cttaaaaagt gtgatggcca    660
actcagcact gcacatgagg ttgttccttt tgcagtgttt aagaactcaa agaaggttta    720
tcttgataag ctggacctga agactgagga gaatctgcta ccagactcat ttgtctgttt    780
cgagcacaaa ggacagtaca aaggaacaat ggactctggt cagactaaga gggagctcaa    840
gtcctttgat atctctcagt gccccaagat tggaggacat ggatcaaaga agtgcactgg    900
ggacgcagca ttttgctctg cttatgagtg cactgctcaa tatgccaatg cctattgttc    960
acatgctaat gggtcaggga ttgttcaaat acaagtatca ggggtctgga agaagccttt   1020
atgtgtaggg tatgagcgcg tggtggtgaa gagagaactc tctgccaagc ccatccagag   1080
agtggagccg tgcacaactt gtataaccaa atgtgagcct catggattgg ttgtcagaag   1140
cacagggttc aagatatcat cagcagttgc ttgtgctagc ggagtctgtg tcacaggatc   1200
gcagagtcct tccaccgaga ttacactcaa gtatccaggt atttcccagt cttctggggg   1260
ggacataggg gttcacatgg cacatgatga ccagtcagtt agctccaaaa tagtagctca   1320
ctgccctccc caggacccct gtttagtgca tgactgcata gtgtgtgctc atggcctgat   1380
caactaccag tgccacactg ctctcagtgc ctttgttgtt gtgtttgtat tctccagcat   1440
tgcaataatt tgtttagcta ttctttatag ggtgcttaag tgcctcaaaa ttgccccaag   1500
gaaagttctg aatccactaa tgtggatcac agctttcatc aggtggatat ataagaagat   1560
ggttgccaga gtggcagaca acatcaacca agtgaacagg gaaataggat ggatggaagg   1620
aggtcagttg gtcctgggaa atcctgcccc tattcctcgt catgccccaa tcccacgtta   1680
tagcacctac ctcatgttat tattgattgt ctcatatgca tcagcatgtt cagaactcat   1740
tcaagcaagc tccagaatca ccacttgctc tacagagggt gtcaacacca aatgtagact   1800
gtctggcaca gcattgatca gagcagggtc agttggagca gaagcttgtt tgatgttgaa   1860
gggggtcaag gaagatcaaa ccaagtttct taaattaaaa actgtctcaa gtgagctatc   1920
atgcagggag ggccagagct actggactgg gtcctttagc cctaaatgtt tgagctcaag   1980
aagatgccac ctggtcgggg aatgccatgt gaataggtgt ctgtcttgga gagacaatga   2040
aacatcagca gagttttcat ttgttgggga aagcacgacc atgagagaaa acaagtgttt   2100
tgagcaatgt ggaggatggg ggtgtgggtg tttcaatgtt aatccatctt gcttatttgt   2160
gcacacgtat ctgcagtcag tgaggaaaga ggcccttaga gtttttaact gtatcgactg   2220
ggtgcataaa ctcaccctgg agatcacaga ctttgatggc tctgtttcaa caatagactt   2280
gggagccagc tccagccgtt tcacaaactg ggttcagtt agcctctcac tggacgcaga    2340
aggaatttca ggctcaaata gcttttcttt cattgagagc ccaggaaaag gatatgcaat   2400
tgttgatgag ccattctcag aaattcctcg gcaaggattt cttggggaga tcaggtgcaa   2460
ttcagagtcc tcagtcctga gtgctcatga gagctgcctt agggcaccaa accttatctc   2520
atacaagccc atgattgacc aattggagtg cacaacaaat ctgattgatc cctttgttgt   2580
ctttgaaaga ggttctctgc cacagacaag gaatgacaaa acctttgcag ccagcaaagg   2640
aaatagaggt gttcaagctt tctctaaggg ctctgtacaa gctgacctca ccctgatgtt   2700
tgacaatttt gaggtggact ttgtgggagc agccgtcagc tgtgatgccg ccttcttaaa   2760
tttgacaggt tgctattctt gcaatgctgg tgccagggtc tgcctgtcta tcacatccac   2820
```

-continued

```
aggaactgga agcctttctg cccacaataa ggatgggtct ctgcatatag tccttccatc   2880
tgaaaatgga acaaaagacc agtgtcagat actacacttc actgtgcctg aagtagaaga   2940
agaatttatg tactcttgtg atggagatga gcggcctctg ttggtcaaag gcaccctgat   3000
agccattgat ccatttgatg ataggcggga agctggaggt gaatcaacag ttgtgaatcc   3060
aaaatctgga tcttggaact tctttgactg gttctctgga ctcatgagtt ggtttggagg   3120
gcctcttaaa actattcttc tcatttgcct gtatgttgca ttatcaattg ggctcttttt   3180
cctcctcatc taccttggag gaacaggcct ctctaaaatg tggcttgctg ccactaagaa   3240
agcttcatag atcagtgcgt gtaaaagcaa tatgttgaag taagtagaca taagctaacc   3300
taattatgta agtattgtac agataggtca aattattgga atatccaagc ttagaaactt   3360
atgcaataat actttagatg taagcttagt tgtaatttgg ggtggtgggg tgaggcagca   3420
gcagtctcaa gtgcttgtga atattctagt tggcgtaatc gtcttttgcc agattagctg   3480
ggaattaaac taactctttg aagttgcacc ggtctttgtg t                        3521
```